US009733180B2

(12) United States Patent
Boutami et al.

(10) Patent No.: US 9,733,180 B2
(45) Date of Patent: Aug. 15, 2017

(54) BOLOMETER WITH HIGH SPECTRAL SENSITIVITY

(71) Applicant: Commissariat a L'Energie Atomique et aux Energies Alternatives, Paris (FR)

(72) Inventors: Salim Boutami, Grenoble (FR); Fabien Eloi, Grenoble (FR); Jerome Hazart, Eybens (FR); Jean-Jacques Yon, Sassenage (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 0 days.

(21) Appl. No.: 15/287,175

(22) Filed: Oct. 6, 2016

(65) Prior Publication Data

US 2017/0102323 A1    Apr. 13, 2017

(30) Foreign Application Priority Data

Oct. 9, 2015 (FR) ..................... 15 59630

(51) Int. Cl.
 *G01N 21/35* (2014.01)
 *G01J 5/34* (2006.01)
 (Continued)

(52) U.S. Cl.
 CPC ............ *G01N 21/3504* (2013.01); *G01J 5/34* (2013.01); *G01J 2005/106* (2013.01)

(58) Field of Classification Search
 CPC ... G01J 2005/106; G01J 5/34; G01N 21/3504
 See application file for complete search history.

(56) References Cited

U.S. PATENT DOCUMENTS

| 2003/0209669 | A1* | 11/2003 | Chou | G01N 21/3504 250/343 |
| 2011/0228809 | A1* | 9/2011 | Tadigadapa | G01K 7/32 374/31 |

(Continued)

FOREIGN PATENT DOCUMENTS

| EP | 0773 435 A2 | 5/1997 |
| FR | 2 977 937 A1 | 1/2013 |

OTHER PUBLICATIONS

French Preliminary Search Report issued Jun. 16, 2016 in French Application 15 59630 filed on Oct. 9, 2015 (with English Translation of Categories of Cited Documents).

*Primary Examiner* — Mark R Gaworecki
(74) *Attorney, Agent, or Firm* — Oblon, McClelland, Maier & Neustadt, L.L.P.

(57) ABSTRACT

A bolometric detector including an absorption membrane, for converting an incident electromagnetic radiation into heat; and a reflector, for reflecting to the absorption membrane part of the incident electromagnetic radiation having passed there through, is provided. The bolometric detector includes a non-metallic layer, situated between the absorption membrane and the reflector, having a series of index jumps, so as to form a network resonating at a wavelength of interest $\lambda_0$; the mean pitch of the network is less than $\lambda_0$; and the optical distance between the absorption membrane and the reflector is substantially equal to a multiple of $\lambda_0/2$.

15 Claims, 4 Drawing Sheets

(51) Int. Cl.
*G01N 21/3504* (2014.01)
*G01J 5/10* (2006.01)

(56) References Cited

U.S. PATENT DOCUMENTS

| | | | |
|---|---|---|---|
| 2012/0235038 A1* | 9/2012 | Nishikawa | G01J 5/0014 |
| | | | 250/338.3 |
| 2013/0051419 A1 | 2/2013 | Chang-Hasnain et al. | |
| 2013/0240738 A1* | 9/2013 | Yon | G01J 5/02 |
| | | | 250/349 |
| 2014/0054462 A1 | 2/2014 | Samarao et al. | |
| 2015/0226612 A1* | 8/2015 | Palanchoke | G01J 5/20 |
| | | | 374/121 |

* cited by examiner

BOLOMETER WITH HIGH SPECTRAL SENSITIVITY

TECHNICAL FIELD

The invention relates to a bolometric detector, that is to say a detector that converts the energy of incident electromagnetic radiation into heat, such that an intensity of this radiation corresponds to a temperature variation.

Bolometric detectors are notably suited to detecting electromagnetic radiation situated in the infrared, in particular at wavelengths comprised between 0.7 μm and 3 mm.

STATE OF THE PRIOR ART

Figure 1A:
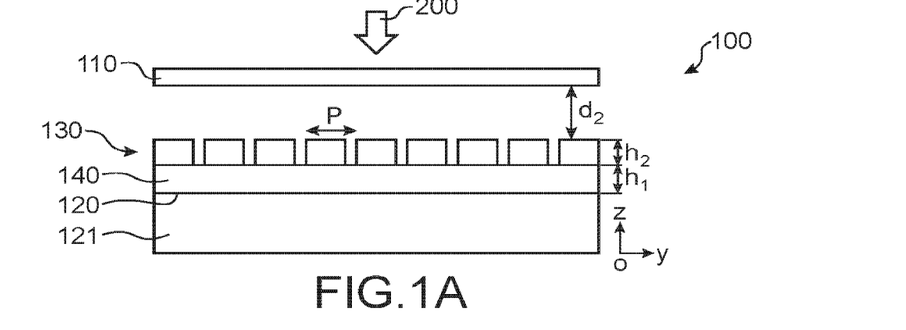
FIGS. 1A and 1B schematically illustrate, along two sectional views, a first embodiment of a bolometric detector according to the invention.

Bolometers as described in FIG. 1A of patent application FR-2977937 are known from the prior art, comprising a membrane forming an absorber-thermistor unit, suspended above a reflector, at a distance $\lambda_0/4$ therefrom, where $\lambda_0$ is the central wavelength of a spectral detection band.

The membrane comprises an absorbing element such as a thin layer of metal, which absorbs an incident electromagnetic radiation and of which the temperature increases in reaction to this absorption, and a thermometric element of which the resistivity varies with temperature.

The reflector and the absorber-thermistor unit together form a quarter-wave cavity enabling high absorption, typically 90%, over a spectral band ranging from 8 to 12 μm or over a spectral band ranging from 3 μm to 5 μm.

A drawback of this bolometer is that it does not offer high spectral selectivity, all the wavelengths being absorbed over a spectral width of several micrometers.

To overcome this drawback, the document proposes depositing, on the membrane forming an absorber-thermistor unit, a metal-insulator-metal stack (MIM structure). At least one lateral dimension of the stack is determined to generate a plasmon resonance with an incident radiation of frequency comprised in said wide spectral band.

A drawback of these stacks deposited on the absorbent membrane is that they increase the thermal mass of the latter, and thus the thermal time constant.

An objective of the present invention is to propose a bolometric detector having high spectral selectivity, and which does not have at least one of the drawbacks of the prior art.

In particular, an aim of the present invention is to propose a bolometric detector having high spectral selectivity, and a thermal mass equivalent to that of the absorber-thermistor unit taken alone.

DESCRIPTION OF THE INVENTION

This objective is attained with a bolometric detector with at least one pixel, each pixel comprising:
- an absorption membrane, suited to converting an incident electromagnetic radiation into heat; and
- a reflector, laid out to reflect to the absorption membrane part of the incident electromagnetic radiation having passed there through.

According to the invention, the bolometric detector has the following characteristics:
- at least one pixel further comprises a non-metallic layer called structured layer, situated between the absorption membrane and the reflector, having a series of index jumps between a first optical index and a second optical index in a plane parallel to the absorption membrane, so as to form a network resonating at a wavelength called wavelength of interest $\lambda_0$;
- the mean pitch of the network is less than said wavelength of interest; and
- the optical distance between the absorption membrane and the reflector is substantially equal to a multiple of $\lambda_0/2$.

The structured layer does not convert an incident electromagnetic radiation into heat, because it is non-metallic.

In the structured layer, each index jump is constituted by an interface between a first material and a second material.

The structured layer forms a resonating network at a wavelength of interest. It is in particular a network called sub-wavelength, the mean pitch of the network being less than said wavelength of interest. In other words, a mean gap between two successive index jumps from the first optical index to the second optical index is less than this wavelength of interest.

Since the network is sub-wavelength, no phenomenon of diffraction is produced therein. At least one part of the incident electromagnetic radiation traverses the absorption membrane and reaches the structured layer where the phenomenon of resonance at the wavelength of interest takes place. A narrow electromagnetic intensity peak is thus formed, centred on the wavelength of interest.

This intensity peak is emitted in the direction of the absorption membrane, and/or in the direction of the reflector which sends it back to the absorption membrane.

This intensity peak is then absorbed by the absorption membrane, which then has a narrow peak of absorbed energy, centred on said wavelength of interest. This peak is called narrow because it has a peak width at half-height less than 150 nm, or even 100 nm, 50 nm, 10 nm or even less.

To this first phenomenon is added a second phenomenon, linked to the optical distance between the absorption membrane and the reflector. The overall spectrum of the power absorbed by the absorption membrane as a function of the wavelength depends on these two phenomena.

In the prior art, the optical distance between the absorption membrane and the reflector is equal to $\lambda_0/4$, to form a cavity resonating over a wide spectral band centred on the wavelength $\lambda_0$.

Here, the optical distance between the absorption membrane and the reflector is substantially equal to a multiple of $\lambda_0/2$, where $\lambda_0$ is the wavelength of interest. Thus, for a wide spectral band centred substantially on $\lambda_0$, an incident electromagnetic radiation on the reflector is in phase opposition with an electromagnetic radiation reflected by the reflector. Consequently, for a wide spectral band centred substantially on $\lambda_0$, the spectrum of the energy absorbed by the absorption membrane has a wide band trough. The trough is called wide band, because it has a peak width at half-height greater than 500 nm, or even 1 μm or even more. This trough corresponds to a low absorption, less than 20%, over a spectral width greater than 100 nm, and even 200 nm, 300 nm or more.

The overall spectrum of the power absorbed by the absorption membrane as a function of the wavelength has both the wide band trough, and the narrow peak, as described above.

Thus, around the wavelength of interest, the absorption membrane has a narrow absorption peak, surrounded on either side by areas of low absorption. Thus, over the spectral band corresponding to the wide band trough, the bolometric detector according to the invention has high spectral sensitivity.

In particular, the bolometric detector according to the invention has, over the spectral band corresponding to the wide band trough, a quality factor greater than 20.

This high spectral selectivity is obtained by means of a shrewd choice of the optical distance between the reflector and the absorption membrane, and a structured layer situated between the two. The structured layer is not deposited on the absorption membrane. Consequently, it does not increase the thermal mass of the absorption membrane. Thus, the bolometric detector according to the invention has a very good thermal time constant, less than those of bolometers with MIM structure described in the introduction.

Moreover, the high spectral selectivity of a pixel of the bolometric detector according to the invention is obtained without it being necessary to place a spectral filter upstream of this pixel.

The wavelength of interest according to the invention is a function of the characteristics of the structured layer. It is thus possible to produce a bolometric detector having two adjacent pixels that are not both sensitive to the same wavelength of interest, without a spectral filter upstream of each pixel.

This thus avoids a luminous radiation filtered by the spectral filter of a first pixel being received by an adjacent pixel (phenomena known as cross-talk).

Moreover, the invention makes it possible to refine further the spectral selectivity of each pixel by means of filters placed upstream. A luminous radiation filtered by the spectral filter of a first pixel, and received by an adjacent pixel, does not produce heating of the absorption membrane of said adjacent pixel, thanks to the intrinsic spectral selectivity of each pixel.

Preferably, a difference between the first optical index and the second optical index is greater than 0.5.

The mean pitch of the network may be comprised between $\lambda_0/2$ and $\lambda_0$, where $\lambda_0$ is the wavelength of interest.

The resonating network is advantageously a periodic network.

In a variant, the resonating network may be a pseudo-periodic network, having variations in the shape of the elementary pattern such as a coverage rate relative to a mean shape of the elementary patterns comprised between 90% and 99%.

The resonating network may have index jumps spread out along the two dimensions of a plane parallel to the absorption membrane.

In a variant, the resonating network may have index jumps spread out along a single dimension of a plane parallel to the absorption membrane.

Each index jump is advantageously constituted of an interface between a first material and a second material, one of said materials being a vacuum or a gas such as air.

Preferably, a gap between the structured layer and the absorption membrane is less than $\lambda_0/2$, where $\lambda_0$ is the wavelength of interest.

The structured layer may be covered with a non-metallic layer called low index layer, spaced apart from the absorption membrane.

The bolometric detector according to the invention advantageously has a plurality of pixels, and at least two pixels differ by their mean shape of the elementary patterns such that they are suited to the detection of different wavelengths of interest.

According to an advantageous embodiment, each pixel has a low index layer, covering the structured layer associated with this pixel and spaced apart from the corresponding absorption membrane, the low index layers each associated with a pixel having different thicknesses.

A non-metallic intermediate layer may extend between the reflector and the structured membrane.

The invention also relates to a gas sensor comprising an infrared source, laid out to emit an electromagnetic radiation inside a cavity, the cavity containing a bolometric detector according to the invention.

BRIEF DESCRIPTION OF THE DRAWINGS

The present invention will be better understood on reading the description of examples of embodiment given for purely indicative purposes and in no way limiting, while referring to the appended drawings in which.

DETAILED DESCRIPTION OF PARTICULAR EMBODIMENTS

FIG. 1A illustrates a first embodiment of a bolometric detector 100 according to the invention.

For reasons of legibility of the figures, only a single pixel of said detector has been represented.

Each pixel comprises an absorption membrane 110 and a reflector 120.

The absorption membrane 110 is constituted of a material suited to converting the energy of an incident electromagnetic radiation into heat, notably an infrared radiation, at a wavelength comprised between 0.7 μm and 3 mm (from the near infrared to the far infrared). The absorption membrane is notably suited to converting wavelengths comprised between 3 μm and 12 μm into heat. The absorption membrane, or bolometric plate, may be made of metal, in particular titanium nitride (TiN). The absorption membrane is continuous in the sense that it does not have holes, in other words its shape is simply connected.

The absorption membrane 110 is in thermal contact with a thermometric element, not represented, making it possible to measure the heating of the absorption membrane. The thermometric element is for example a layer of a material having a strong variation in resistivity as a function of temperature, deposited directly on the absorption membrane. The thermometric element is for example made of vanadium oxide.

The reflector 120, or mirror, is constituted of a reflective surface facing the absorption membrane. The reflector 120 may be formed of a reflective treatment deposited on a substrate 121. The reflector is reflective to the wavelengths to which the absorption membrane is absorbent. It may be constituted of a very thin metal layer, for example a layer of copper or aluminium of 50 nm thickness.

The reflector 120 extends parallel to the absorption membrane 110, on the side opposite to a source emitting the electromagnetic radiation 200.

The reflector 120 and the absorption membrane 110 are known elements of a bolometric detector, which is why they are not described further herein.

At least one pixel of the bolometric detector according to the invention, preferably all, have the additional characteristics as described hereafter, so as to have high spectral sensitivity.

A layer called structured layer 130, non-metallic, is interposed between the reflector 120 and the absorption membrane 110, at a distance from each of these two elements.

The absorption membrane 110 is suspended above the structured layer 130 by support means, thermally insulating, not represented.

In particular, the distance $d_2$ between the structured layer and the absorption membrane is greater than $\lambda_0/10$, where $\lambda_0$ is the central wavelength of an absorption peak of the pixel of the bolometric detector, called wavelength of interest. More details on this wavelength are given hereafter.

The distance $d_2$ is measured from the upper face of the structured layer 130, on the side of the absorbent membrane, up to the lower face of the absorbent membrane 110, on the side of the structured layer.

The structured layer 130 is thermally insulated from the absorption membrane 110, notably by a layer of a vacuum or a gas such as air.

Without precision on the pressure, a layer of a gas such as air designates a layer at the pressure of the surrounding air, i.e. generally 1.013 bar.

Throughout the text, a vacuum designates a volume of a gas such as air, having a pressure strictly less than 1 bar, for example less than 0.5 bar, less than 50 mbar or less.

In the example illustrated here, this layer of a vacuum or a gas such as air has a thickness equal to the distance $d_2$.

The structured layer is moreover at a distance from the reflector.

Preferably, it is in direct physical contact with a same material, on the side of the reflector and on the side of the absorption membrane.

The structured layer 130 is here constituted of a network made of a first material, having an optical index $n_{2h}$, the troughs of the network being filled by a material of optical index $n_{2b}$ strictly less than $n_{2h}$.

Here, the troughs of the network made of material of optical index $n_{2h}$ are filled by a vacuum. In a variant, they are filled by a gas such as air, or by another solid material.

Preferably, the height of the trough of the network made of material of index $n_{2h}$ is equal to the thickness of the structured layer 130 (dimension along the axis (Oz) defined hereafter). Here, the structured layer has a thickness $h_2$=380 nm.

It may be considered that the structured layer 130 is constituted of two interwoven mono-material networks of index $n_{2h}$ respectively $n_{2b}$, the material of index $n_{2b}$ being a vacuum, or a gas such as air or a solid material. The structured layer may then be considered as a bi-material network.

In other words, the structured layer 130 may be considered as a membrane of high index structured with a medium of low index, or as a network constituted of an alternation of non-metallic materials with a contrast of index such that $n_{2b}<n_{2h}$ (in particular $n_{2b}<n_{2h}-0.5$, as detailed hereafter).

Throughout the text, an optical index designates a refractive index at the wavelength of interest.

The structured layer 130 is thus defined by a series of index jumps between the optical index $n_{2h}$ and the optical index $n_{2b}$. These index jumps are spread out in planes parallel to the absorption array 110. Thus, the structured layer does not form a network of Bragg network type, but a network having structurings distributed over a plane parallel to the absorption array.

In the example illustrated here, the structured layer 130 is constituted of a network made of amorphous silicon, the trough of the network being filled by a vacuum. This thus gives $n_{2h}$=3.6, and $n_{2b}$=1.

Numerous variants may be implemented without going beyond the scope of the invention, preferably verifying $n_{2h}-n_{2b}>0.5$, and in an even more preferred manner $n_{2h}-n_{2b}>1$. Moreover, preferably $n_{2h}>1.5$, and even $n_{2h}>3$ are verified.

The material of index $n_{th}$ may be amorphous silicon or germanium. The material of optical index $n_{2b}$ may be a vacuum, a gas such as air, silica, zinc sulphide, a nitride.

The structured layer 130 forms a network resonating at the wavelength of interest $\lambda_0$.

The structured layer 130 is a resonant structure, which sends to the absorption membrane 130 and/or to the reflector, an electromagnetic radiation having an intensity peak centred on the wavelength of interest $\lambda_0$. This peak is narrow, of peak width at half-height less than, for example, 50 nm. This intensity peak is named resonance at the wavelength of interest.

The resonance at the wavelength of interest is sent back to the absorption membrane, directly, or indirectly via the reflector 120.

The term concentrating membrane may be used to designate the structured layer 130, or integrated filtering structure.

This resonance is absorbed by the absorbent membrane 110. The absorption may implement an evanescence phenomenon.

In order that the resonance is absorbed as best as possible by the absorbent membrane 110, the thickness $d_2$ defined above is preferably less than $\lambda_0/2$. This then gives $\lambda_0/10<d_2<\lambda_0/2$. In the example represented here, $d_2$=2000 nm.

The structured layer 130 here forms a periodic resonating network, such that the pitch P of the network is less than the wavelength of interest $\lambda_0$.

Notably $\lambda_0/2<P<\lambda_0$.

It is more particularly a network having second-order periodicity.

FIG. 1A shows a pixel of the bolometric detector along a section in a plane parallel to the plane (zOy), where (Oz) is an axis orthogonal to the plane of the absorbent membrane, and (Oxyz) an orthonormal reference point.

Figure 1B:
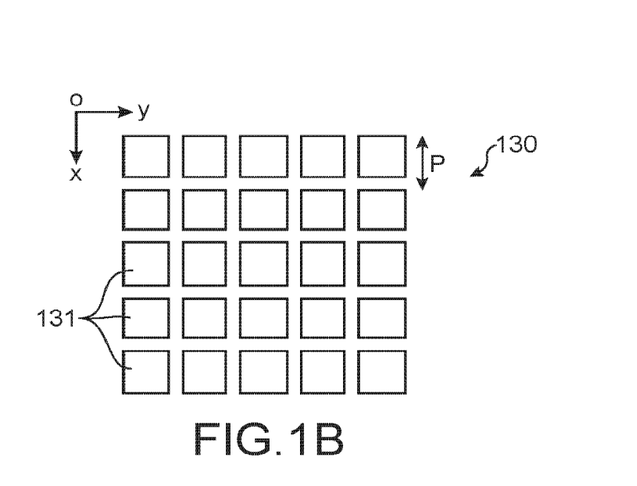

FIG. 1B shows this pixel along a sectional view in a plane parallel to the plane (x0y) passing through the structured layer 130.

In the example illustrated here, the structured layer 130 has a periodicity along two dimensions (along (Ox) and (Oy)), and the pitch is the same along these two dimensions.

The structured layer 130 is here formed of pads 131 constituted of the material of index $n_{2h}$, the pads being separated by empty interstices.

A fill factor per unit volume may be defined, corresponding to the ratio between the volume occupied by the material of index $n_{2h}$ in the structured layer 130 and the total volume of the structured layer 130. The pads being with square base, the focus here will rather be made on a fill factor per unit length, corresponding to the ratio between the width L of this square and the pitch P of the network. The fill factor per unit length is here equal to 0.85.

In order to maintain the structured layer 130 at a distance from the reflector, it is deposited on an intermediate layer 140, itself deposited on the reflector. The intermediate layer 140 assures a mechanical maintaining of the structured layer 130, notably when the space between the pads is filled by a vacuum or a gas such as air.

The intermediate layer 140 is in direct physical contact with the reflector 120 on one side, and the structured layer 130 on the other side. It preferably has a range at least equal to that of the structured layer 130.

The intermediate layer 140 is made of solid material. It is made of non-metallic material, here of zinc sulphide (ZnS), of index $n_1=2.2$. In a variant, it may be made of silica, nitride (or constituted of a vacuum or a gas such as air as illustrated hereafter).

It here has a thickness $h_1=620$ nm.

The intermediate layer 140 forms a homogenous layer of index $n_1$ less than $n_{2h}$, with preferably $n_{2h}-n_1>0.5$, and in an even more preferred manner $n_{2h}-n_1>1$. Preferably, $n_1<2$.

The optical distance between the absorbent membrane 110 and the reflector 120 is substantially equal to a multiple of $\lambda_0/2$. "Substantially" is taken to mean comprised between more or less 15% of $\lambda_0/2$, around a multiple of $\lambda_0/2$, preferably 10% and even 5%. In other words, each pixel of the bolometric detector forms a cavity of optical thickness $N*\lambda_0/2$, with N a positive integer.

This optical distance is measured from the lower face of the absorbent membrane, on the side of the reflector, up to the upper face of the reflector, on the side of the absorbent membrane.

An optical distance is defined by the product of a length and an optical index, in particular a mean optical index when an optical distance is considered along the axis (Oz), in the structured layer 130.

Here, the optical distance between the absorbent membrane 110 and the reflector 120 is approximately defined by:

$$D1=h_1*n_1+h_2*[F*n_{2h}+(1-F)*n_{2b}]+d_2*n_{gap}$$

with $n_{gap}$ the index in a layer of air or vacuum situated between the absorbent membrane and the structured layer, and F the fill factor per unit volume defined above.

With the values given above, $D1=4.45$ μm$\approx\lambda_0$ is obtained.

As explained in the description of the invention, this optical distance is at the origin of a practically zero absorption around $\lambda_0$, over a wide spectral band, except for the narrow absorption peak generated by the resonance of the structured layer 130.

Figure 2:
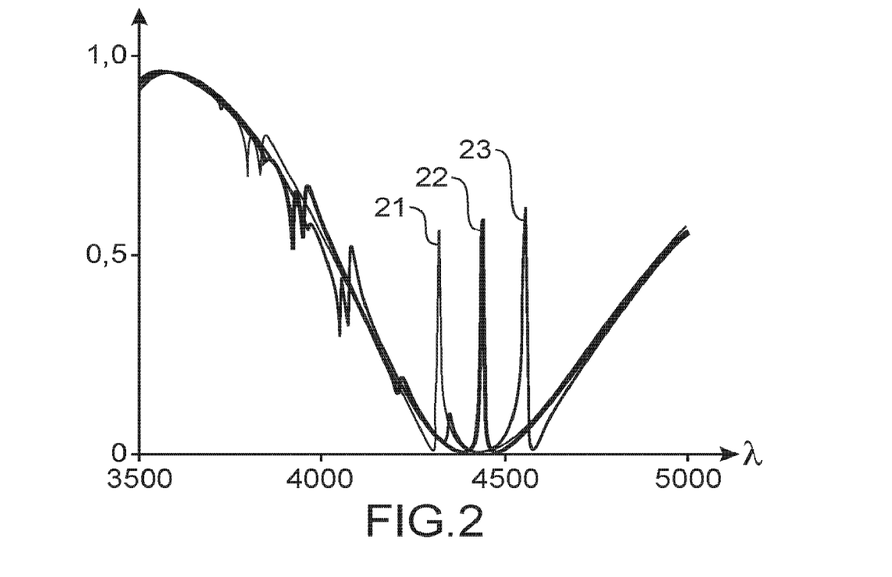
FIG. 2 illustrates absorption spectra of bolometric detectors of the type of that of FIGS. 1A and 1B.

FIG. 2 illustrates the absorption spectra 21, 22, 23 of bolometric detectors of the type of that of FIGS. 1A and 1B, which only differ by the pitch P in the structured layer 130.

The x-axis is a wavelength in nm. The y-axis is a normed absorption rate.

As expected, each spectrum has a narrow peak of peak width at half-height less than 50 nm, for example 10 nm, and an absorption trough centred on 4.45 μm (=D1).

The absorption trough has a peak width at half-height of around 1 μm (width of the trough at a value of the absorption equal to half of the peak-valley amplitude of the absorption trough). This absorption trough corresponds as a first approximation to the complementary of the wide band absorption peak of a bolometric detector according to the prior art as described in the introduction.

In operation, the electromagnetic radiation 200 incident on the bolometric detector has a spectral range comprised in this absorption trough. For example, this radiation is emitted by a wide band source, of which the emission band is comprised in the absorption trough. In a variant, a very wide band radiation is emitted, then filtered by a spectral filter of which the transmission band lies within the absorption trough.

Thus, a pixel of the bolometric detector uniquely detects variations in intensity at the wavelength of the absorption peak, without being perturbed by the absorption at neighbouring wavelengths, which is practically zero.

A detection at very high spectral sensitivity is thus obtained, thanks to the narrow peak situated in an absorption trough.

The absorption spectrum 21 corresponds to P=3750 nm. The narrow peak of the spectrum 21 is centred on a first wavelength of interest $\lambda_{01}$ equal to 4350 nm.

The optical distance D1 indeed verifies the condition expressed above, in particular: $D1=N*(\lambda_{01}/2)-(\lambda_{01}/2)*4.6\%$, with N=2.

The absorption spectrum 22 corresponds to P=3900 nm. The narrow peak of the spectrum 22 is centred on a second wavelength of interest $\lambda_{02}$ equal to 4450 nm.

The optical distance D1 indeed verifies the condition expressed above, in particular: $D1=N*(\lambda_{02}/2)$, with N=2.

The absorption spectrum 23 corresponds to P=4050 nm. The narrow peak of the spectrum 23 is centred on a third wavelength of interest $\lambda_{03}$ equal to 4550 nm.

The optical distance D1 indeed verifies the condition expressed above, in particular: $D1=N*(\lambda_{03}/2)+(\lambda_{03}/2)*4.4\%$, with N=2.

FIG. 2 illustrates the fact that the characteristics of the structured layer 130 make it possible to adapt the characteristics of the narrow absorption peak.

In particular, the pitch of the resonating network forming the structured layer makes it possible to define the wavelength of interest $\lambda_0$.

It is thus possible to produce a bolometric detector with several pixels, in which several pixels have the characteristics of the invention, but are not all associated with the same wavelength of interest.

In particular, two adjacent pixels may each be sensitive to a different wavelength of interest, without it being necessary that each pixel is covered by a distinct spectral filter. Cross-talk phenomena are thus avoided, due notably to the diffraction of light on the edge of a filter, when two different filters are arranged above two adjacent pixels. Moreover, the invention enables detections at two different wavelengths simultaneously.

It is notably possible to produce a bolometric detector constituted of an array of different types of pixels that differ by their wavelength of interest, spread out according to a periodic layout, with an elementary pattern comprising at least one pixel of each type. The pixels are then spread out in groupings of pixels, each grouping corresponding to an elementary pattern.

For example, the different types of pixels are distributed according to a Bayer array. Thus, not all the types of pixels are necessarily present in the same number, and the proportion of each type of pixel makes it possible to give more or less weight to certain wavelengths of interest.

A multi-spectral imager is thereby produced, supplying several interleaved images, each associated with a particular wavelength, the interlaced images together forming a multi-spectral image. Such an imager may be suited to the acquisition of an image of a nocturnal scene.

FIG. 2 also illustrates the fact that for small variations in the wavelength of interest, from one pixel to the next, the optical distance D1 may remain the same from one pixel to the next. These small variations are for example variations less than 300 nm, or even 200 nm.

Figure 3A:
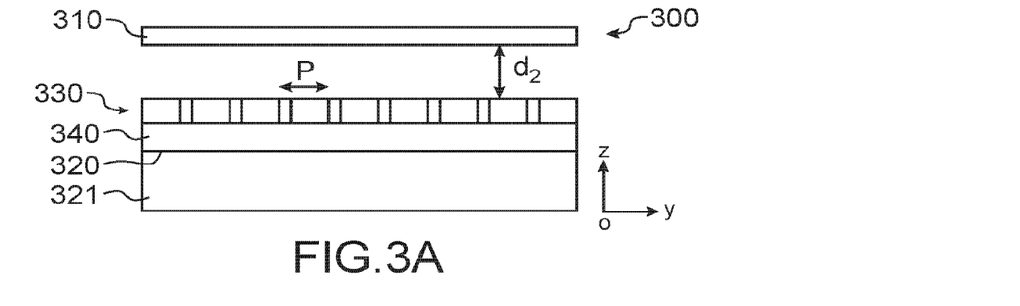
FIGS. 3A and 3B schematically illustrate, along two sectional view, a second embodiment of a bolometric detector according to the invention.
Figure 3B:
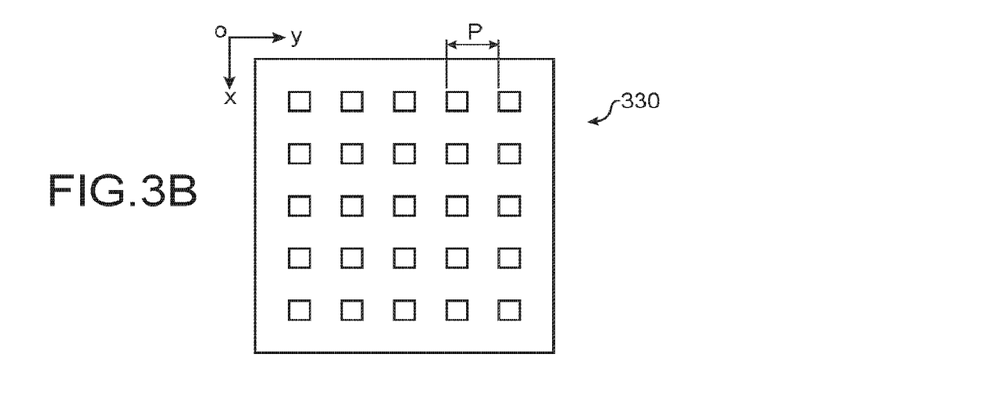

FIGS. 3A and 3B schematically illustrate a second embodiment of a bolometric detector 300 according to the invention.

The numerical references of FIGS. 3A and 3B correspond to those of FIGS. 1A and 1B, the figure of hundreds being replaced by a 3.

The second embodiment of a bolometric detector only differs from the first embodiment in that the structured layer 330 is a grid of through holes. The through holes each have a square section in the plane (xOy), and are distributed over this plane according to a periodic grid in two dimensions of pitch P.

The fill factor per unit length is here equal to 0.25. The distance $d_2$ is adjusted such that the optical distance D1 between the reflector 320 and the structured layer 310 is always equal to 4.45 µm.

Figure 4:
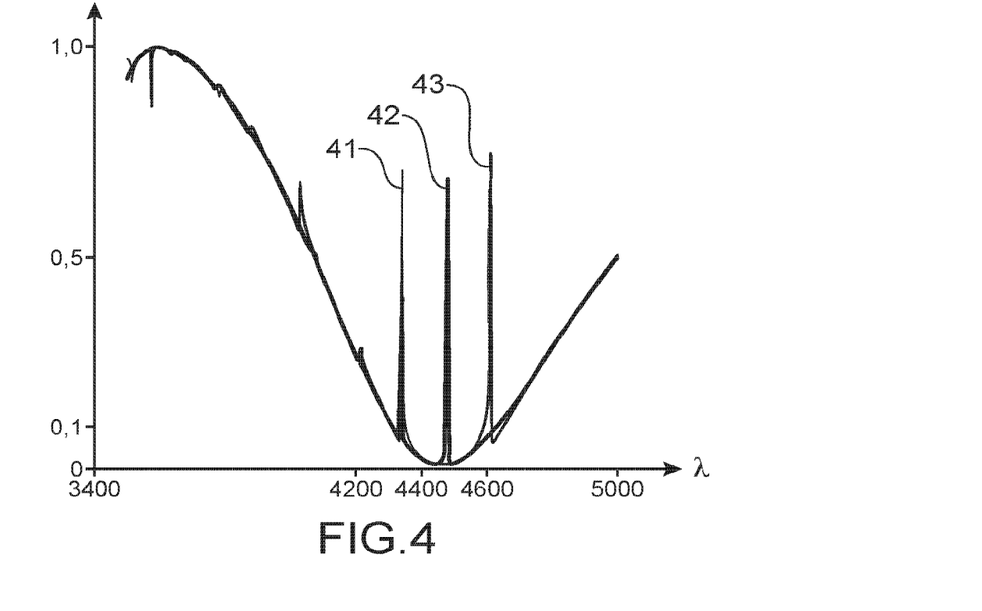
FIG. 4 illustrates absorption spectra of bolometric detectors of the type of FIGS. 3A and 3B.

The graph of FIG. 4 corresponds to that of FIG. 2.

The spectrum 41 corresponds to a pitch P=3450 nm, the spectrum 42 corresponds to a pitch P=3600 nm, the spectrum 43 corresponds to a pitch P=3750 nm.

Results similar to those obtained with the first embodiment are obtained, the narrow peaks being even thinner (peak width at half-height of only several nm, around 5 nm).

Figure 5A:
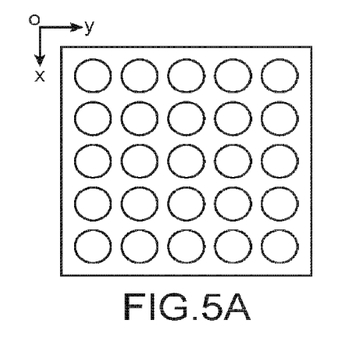
FIGS. 5A to 5C illustrate different variants of a structured layer of a bolometric detector according to the invention.
Figure 5B:
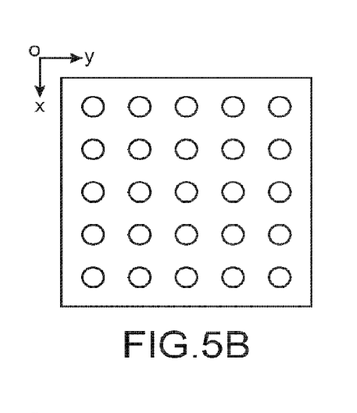
Figure 5C:
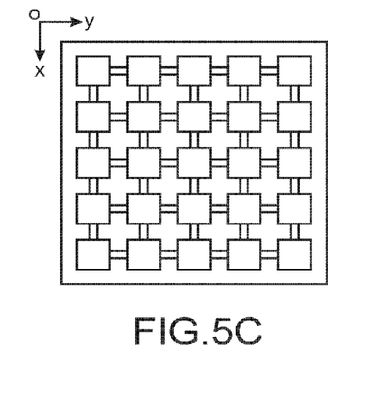

FIGS. 5A to 5C illustrate different variants of a structured layer of a bolometric detector according to the invention.

In FIG. 5A, the structured layer is constituted of a network of cylindrical pads with circular base, distributed according to a square grid.

The fill factor per unit length is equal to 0.85, and the distance D1 is equal to 4.45 µm. For pitches P=3300 nm, P=3450 nm, and P=3600 nm, absorption spectra of the types of those of FIG. 2 are obtained, except that the peak width at half-height is wider, of the order of 50 nm.

In FIG. 5B, the structured layer is constituted of a grid of through holes. The through holes each have a circular section in the plane (xOy), and are distributed over this plane according to a periodic grid in two dimensions.

The fill factor per unit length is equal to 0.25, and the distance D1 is equal to 4.45 µm. For pitches P=3450 nm, P=3600 nm, and P=3750 nm, absorption spectra of the type of those of FIG. 3 are obtained.

In FIG. 5C, the structured layer is constituted of a network of pads with square base, of the type of that illustrated in FIG. 1B, the pads being connected two by two by narrow bridges.

The pads are distributed along lines parallel to (Ox) and along columns parallel to (Ox). Each narrow bridge extends parallel to (Ox) or to (Oy), along an axis connecting the centres of two neighbouring pads. Each pad is connected to the neighbouring pad situated below, above, to the right and to the left (if this neighbour exists).

The narrow absorption peak depends on the characteristics of the structured layer. As detailed above, a network pitch makes it possible to adjust the wavelength of interest (central wavelength of the peak). Other parameters also make it possible to adjust the wavelength of interest and/or the spectral width of the peak. These parameters are notably the fill factor per unit length or per unit volume, the section of the pads, the thickness of the structured layer, the shape of the pads, etc. These parameters are characteristics of the shape of an elementary pattern of the network formed by the structured layer.

For example, a network of pads with circular base has an absorption peak of greater spectral width than a network of pads with square base. Similarly, the fill factor per unit length of a network of pads makes it possible to adjust the spectral width of the absorption peak.

Figure 6:
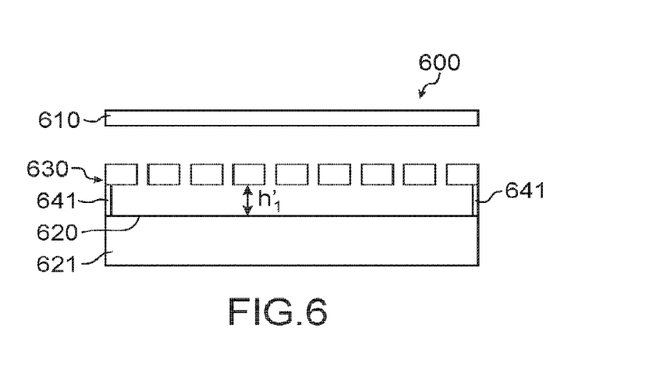
FIG. 6 schematically illustrates a third embodiment of a bolometric detector according to the invention.

FIG. 6 schematically illustrates a third embodiment of a bolometric detector 600 according to the invention.

The numerical references of FIG. 6 correspond to those of FIG. 3A, the figure of hundreds being replaced by a 6.

The third embodiment of a bolometric detector only differs from the second embodiment in that the structured layer 630 is held suspended above the reflector, without direct physical contact with the reflector.

To maintain the structured layer 630 suspended, pillars 641 are arranged between the structured layer 630 and the reflector 620.

The structured layer 630 and the reflector 620 are then separated by a layer of air or a vacuum, of height $h_1'$, with here $h_1'$=620 nm.

This embodiment is suited when the structured layer is formed by a grid of through holes, or by pads connected together by narrow bridges, or by two interwoven mono-material networks, each network being constituted of a solid material.

This embodiment is obtained by means of a sacrificial layer which is removed after production of the structured layer 630.

It establishes a symmetry on either side of the structured layer (same material on each side), making it possible to obtain a total absorption at the wavelength of interest.

Figure 7:
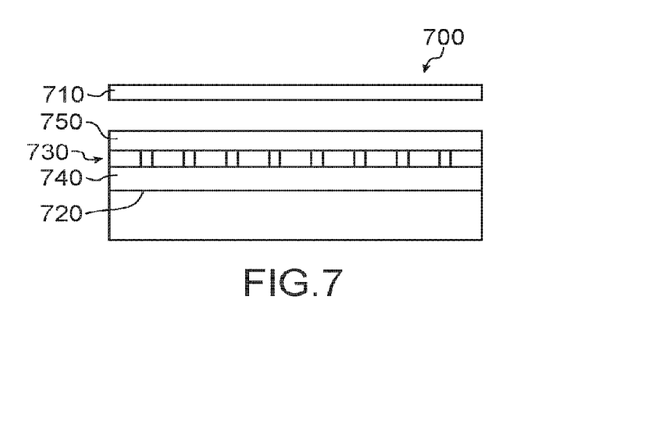
FIG. 7 schematically illustrates a fourth embodiment of a bolometric detector according to the invention.

FIG. 7 schematically illustrates a fourth embodiment of a bolometric detector 700 according to the invention.

The numerical references of FIG. 7 correspond to those of FIG. 3A, the figure of hundreds being replaced by a 7.

The fourth embodiment of a bolometric detector only differs from the second embodiment in that the structured layer 730 is covered by a non-metallic layer called low index layer 750.

The low index layer is in direct physical contact with the structured layer 730, and separated from the absorption membrane 710 by a layer of air or a vacuum. This low index layer 750 has an optical index $n_3<n_{2h}$, with preferably $n_{2h}-n_3>0.5$, and even $n_{2h}-n_3>1$.

Preferably, the low index layer is constituted of the same material as the intermediate layer 740.

It may further have the same thickness as the intermediate layer 740.

The low index layer 750 makes it possible to conserve a symmetry on either side of the structured layer (same material on each side), when the structured layer is deposited on an intermediate layer made of solid material. Such symmetry makes it possible to obtain a total absorption at the wavelength of interest.

The low index layer 750 also makes it possible to protect the structured layer 730.

It is particularly suited when the structured layer is constituted of two interwoven mono-material networks, each network being constituted of a solid material.

It has an optical index greater than that of a vacuum or air, which makes it possible if need be to reduce a total height of the bolometric detector according to the invention for a same optical distance D1 between the reflector 720 and the absorption membrane 710.

Another advantage of this low index layer is detailed hereafter.

Figure 8A:
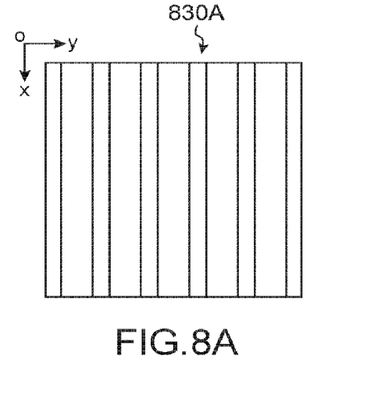
FIGS. 8A and 8B illustrate two other variants of a structured layer of a bolometric detector according to the invention.
Figure 8B:
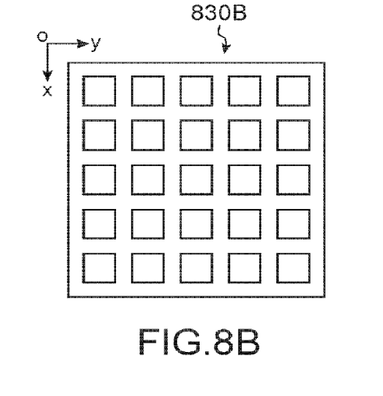

FIGS. 8A and 8B illustrate two other variants of a structured layer of a bolometric detector according to the invention.

In FIG. 8A, the structured layer 830A forms a periodic resonating network along a single direction. It is a network of the network of hatchings type.

This variant is suited when the electromagnetic radiation to detect is polarised, notably according to a rectilinear polarisation.

In FIG. 8B, the structured layer 830B forms a pseudo-periodic resonating network.

A pseudo-periodic network is a periodic network, in which the elementary patterns have slight variations relative to each other.

It involves variations in the shape of an elementary pattern, for example a variation in the total width of a pattern (pitch of the network), a variation in a fill factor per unit length or per unit volume (for example variation in the width of the pads), and/or a variation in the shape of a pad or of a hole traversing a grid.

These variations are limited. In particular, the coverage rate of each elementary pattern, relative to a mean shape of the elementary patterns, is comprised between 90% and 99%, and even between 95% and 99%.

In the example illustrated in FIG. 8B, the pads are distributed substantially according to a square grid, the spacing between two pads along the axis (Oy) varying slightly from one pad to the other. The network pitch along (Oy) has variations comprised between 1% and 10%, relative to a mean network pitch along (Oy). For reasons of legibility of the figure, the differences are exaggerated in FIG. 8B.

In FIG. 8B, the structured layer forms a pseudo-periodic network along two dimensions.

In a variant, the structured layer may form a pseudo-periodic network along a single dimension (of the network of hatchings type with slight variations from one hatching to another).

In a pseudo-periodic network, the absorption peak is a function of the mean parameters of the elementary pattern, for example the mean network pitch, the mean fill factor per unit length or per unit volume, a mean shape of the pads, etc.

This absorption peak is also a function of the standard deviation on these mean parameters, from one elementary pattern to the other. The greater this standard deviation, the more the absorption peak has a wide spectral width.

For example, it is possible to fix the wavelength of interest by means of the mean network pitch, and the spectral width of the absorption peak by means of the standard deviation on the network pitch, from one elementary pattern to the other.

Thus, the structured layer according to the invention may form a periodic or pseudo-periodic network along two dimensions (having second order periodicity), or a periodic or pseudo-periodic network along one dimension (having first order periodicity).

Figure 9:
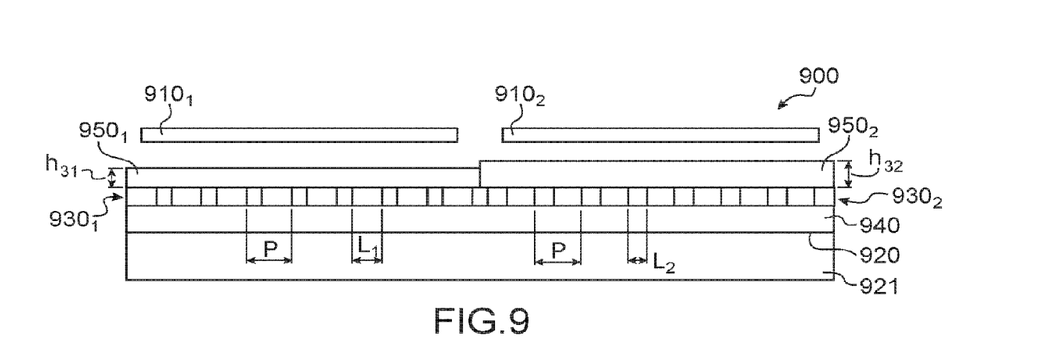
FIG. 9 schematically illustrates two pixels of a fifth embodiment of a bolometric detector according to the invention.

FIG. 9 schematically illustrates two pixels of a fifth embodiment of a bolometric detector 900 according to the invention.

Each pixel will only be described for its differences relative to the pixel of the fourth embodiment.

The numerical references of FIG. 9 correspond to those of FIG. 7, the figure of hundreds being replaced by a 9.

The two pixels represented are two pixels of a matrix bolometric detector, constituted of a plurality of pixels.

The pixels share a same substrate 921, a same reflector 920, and a same intermediate layer 940, each formed of a single piece over the whole extent of the array of pixels.

In a variant, each pixel comprises a distinct reflector.

Each pixel has its own absorption membrane $910_1$, respectively $910_2$, and its own structured layer $930_1$, respectively $930_2$.

The respective structured layers each form a resonating network of fill factor per unit length $L_1/P$, respectively $L_2/P$.

The two adjacent pixels are thus each suited to the detection of a different wavelength of interest $\lambda_{o1}$, respectively $\lambda_{o2}$.

Each structured layer $930_1$, respectively $930_2$, is covered with a corresponding low index layer $950_1$, respectively $950_2$.

The thickness $h_{31}$, respectively $h_{32}$ of each low index layer is adapted such that in each pixel, the optical distance between the reflector and the absorption membrane is substantially equal to a multiple of half of the wavelength of interest.

In particular, $h_{31}$ is adapted so that this optical distance in the pixel on the left is substantially equal to a multiple of $\lambda_{o1}/2$, and $h_{32}$ is adapted to that this optical distance in the pixel on the right is substantially equal to a multiple of $\lambda_{o2}/2$.

The low index layer thus makes it possible that, in a multi-spectral bolometric detector, all the absorption membranes are situated in a same plane, all the reflectors are situated in a same plane, and that in each pixel the optical distance between the reflector and the absorption membrane is adjusted to the wavelength of interest associated with this pixel.

This embodiment is particularly suited when the pixels of a same bolometric detector are associated with wavelengths that differ by more than 200 nm, and even more than 300 nm.

The bolometric detector according to the invention finds particular interest for the detection of gases (spectroscopy in the infrared), while making it possible that each pixel of the detector is only sensitive over a spectral range characteristic of a gaseous species. It is thus possible to produce gas sensors having an excellent signal to noise ratio.

Figure 10:
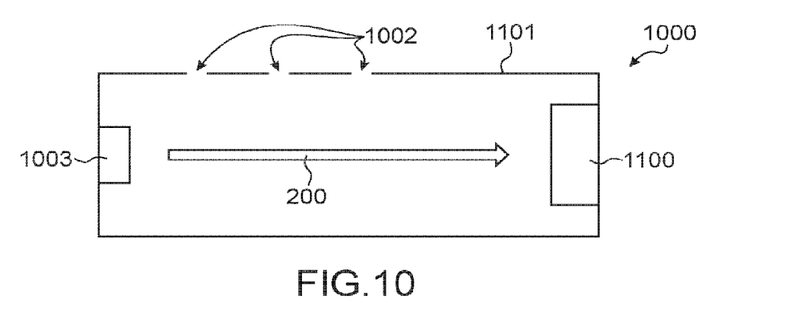
FIG. 10 schematically illustrates a gas sensor including a bolometric detector according to the invention.

FIG. 10 illustrates a gas sensor 1000 comprising a cavity 1001 provided with openings 1002 to allow a gas to enter.

An infrared source 1003 of black body type emits an electromagnetic radiation 200 inside this cavity. The source is called black body type because it emits an infrared radiation at a wavelength that is a function notably of its temperature. In particular, the source emits a wide band radiation, over a spectral band ranging from 3 µm to 5 µm. In a variant, it emits a radiation over a spectral band ranging from 8 µm to 12 µm. A filter may be arranged at the outlet of the source, to select a narrower spectral band, for example of spectral width 1 µm.

A bolometric detector 1100 according to the invention is arranged inside the cavity, facing the infrared source.

The spectral range of the wide band radiation emitted inside the cavity corresponds to the spectral range of the absorption trough of the bolometric detector.

The electromagnetic radiation 200 emitted by the infrared source traverses the cavity filled with a gas.

The gas absorbs in a narrow spectral band of peak width at half-height generally less than 300 nm. Said spectral band is characteristic of a gas. Thus, by identifying the spectral band(s) absorbed inside the cavity 1001, it is possible to identify the gas or gases present in the cavity.

The bolometric detector comprises several pixels, each associated with an absorption peak centred on a different wavelength of interest. Each wavelength of interest corresponds to a central wavelength of an absorption characteristic of a gas.

Thanks to the high spectral sensitivity of the bolometric detector according to the invention, a gas may be identified in a very reliable manner, and it is possible to determine in a precise manner its concentration inside the cavity 1001 by measuring a relative signal variation.

Thanks to the narrow absorption peak situated in a practically zero absorption area, a pixel of the bolometric detector only absorbs in the absorption spectral band of the gas, and does not absorb a continuous background due to all the wavelengths emitted by the source and not absorbed by the gas. The relative variation in signal as a function of a concentration of this gas will thus be much stronger than with bolometers according to the prior art.

The invention also has a particular interest in that it enables simultaneous detection of multiple gases. To do so, a bolometric detector is produced with several pixels (or groups of pixels), each sensitive respectively to one of the gases. It is thus possible to determine easily the different concentrations of the different gases. Bolometers of the prior art are incapable of working back to the concentration of each gas, because they are sensitive to all gases at the same time, and different combinations of concentrations of gas will give the same signal on the bolometer.

Other advantageous uses may be implemented, for example imagers, in particular nocturnal vision imagers.

The invention claimed is:

1. A bolometric detector including at least one pixel, the at least one pixel comprising:
   an absorption membrane configured to convert incident electromagnetic radiation into heat;
   a reflector configured to reflect to the absorption membrane part of the incident electromagnetic radiation having passed through the absorption membrane; and
   a non-metallic structured layer disposed between the absorption membrane and the reflector and being thermally insulated from the absorption membrane, the structured layer having a series of optical index jumps between a first optical index and a second optical index in a plane parallel to an upper surface of the absorption membrane, forming a resonating network at a wavelength of interest ($\lambda_0$),
   wherein a mean pitch of the resonating network is less than $\lambda_0$, and
   wherein an optical distance between the absorption membrane and the reflector is substantially equal to a multiple of $\lambda_0/2$.

2. The bolometric detector according to claim 1, wherein a difference between the first optical index and the second optical index is greater than 0.5.

3. The bolometric detector according to claim 1, wherein the mean pitch of the network is between $\lambda_0/2$ and $\lambda_0$.

4. The bolometric detector according to claim 1, wherein the resonating network is a periodic network.

5. The bolometric detector according to claim 1,
   wherein the resonating network is a pseudo-periodic network, having variations in a shape of an elementary pattern of said resonating network, and
   wherein a coverage rate of the elementary pattern relative to a mean shape of the elementary pattern is between 90% and 99%.

6. The bolometric detector according to claim 1, wherein the optical index jumps are distributed along directions corresponding to two perpendicular directions in the plane parallel to the absorption membrane.

7. The bolometric detector according to claim 1, wherein the optical index jumps are distributed along a direction corresponding to a single direction in the plane parallel to the absorption membrane.

8. The bolometric detector according to claim 1,
   wherein each index jump in said series is constituted by an interface between a first material and a second material, and
   wherein one of the first and second materials is a vacuum or a gas.

9. The bolometric detector according to claim 1, wherein a gap between the structured layer and the absorption membrane is less than $\lambda_0/2$.

10. The bolometric detector according to claim 1, further comprising a low-index layer covering the structured layer and being spaced apart from the absorption membrane.

11. The bolometric detector according to claim 1, wherein the at least one pixel comprises a plurality of pixels, at least two pixels in said plurality differing by a mean shape of elementary patterns and being configured to detect different wavelengths of interest.

12. The bolometric detector according to claim 11, wherein each pixel in said plurality includes a corresponding low-index layer covering the structured layer of said each pixel and being spaced apart from a corresponding absorption membrane of said each pixel, a thickness of each corresponding low-index layer being chosen so as to maintain an optical distance between the corresponding absorption membrane and a corresponding reflector that is substantially equal to a multiple of $\lambda_0/2$.

13. The bolometric detector according to claim 12, wherein at least two of said each corresponding low-index layer have thicknesses that are different from each other.

14. The bolometric detector according to claim 1, further comprising an intermediate non-metallic layer extending between the reflector and the structured layer.

15. A gas sensor comprising an infrared source configured to emit an electromagnetic radiation inside a cavity, wherein the cavity contains a bolometric detector according to claim 1.

* * * * *